United States Patent
Kwak et al.

(10) Patent No.: US 11,776,665 B2
(45) Date of Patent: Oct. 3, 2023

(54) METHOD FOR DETERMINING THE AVERAGE DEUTERIUM SUBSTITUTION RATE

(71) Applicant: LG Chem, Ltd., Seoul (KR)

(72) Inventors: Sooyoung Kwak, Daejeon (KR); Eunhee Kim, Daejeon (KR); Young Hee Lim, Daejeon (KR); Yu Ra Lee, Daejeon (KR)

(73) Assignee: LG Chem, Ltd.

( * ) Notice: Subject to any disclaimer, the term of this patent is extended or adjusted under 35 U.S.C. 154(b) by 282 days.

(21) Appl. No.: 17/307,455

(22) Filed: May 4, 2021

(65) Prior Publication Data

US 2021/0350882 A1 Nov. 11, 2021

(30) Foreign Application Priority Data

May 11, 2020 (KR) .................. 10-2020-0056067
Dec. 16, 2020 (KR) .................. 10-2020-0176587

(51) Int. Cl.
*G16C 20/20* (2019.01)
*G01R 33/46* (2006.01)

(52) U.S. Cl.
CPC .......... *G16C 20/20* (2019.02); *G01R 33/4625* (2013.01)

(58) Field of Classification Search
None
See application file for complete search history.

(56) References Cited

U.S. PATENT DOCUMENTS

2018/0198080 A1   7/2018   Noh et al.

FOREIGN PATENT DOCUMENTS

| JP | 2009269825 A | 11/2009 |
| JP | 2010256104 A | 11/2010 |
| KR | 100371908 B1 | 2/2003 |
| KR | 20170025869 A | 3/2017 |
| KR | 20180082808 A | 7/2018 |
| KR | 20190050432 A | 5/2019 |

OTHER PUBLICATIONS

Deuterium Exchange of Organic and Organosilicon Compounds on Group VIII Transition Metals, 1983, University of New South Wales (Year: 1983).*
Benzo[a]pyrene Diol Epoxide Forms Covalen Adducts with Deoxycytidylic Acid by Alkylation at Both Exocyclic Amino N4 and Ring Imino N-3 Positions Chem. Res. Toxicol. 2004, 17, 4, 476-491 (Year: 2004).*

* cited by examiner

*Primary Examiner* — Roy Y Yi
(74) *Attorney, Agent, or Firm* — Lerner David LLP

(57) ABSTRACT

The present disclosure relates to a method for analysis of an average deuterium substitution rate of a deuterium-substituted sample using information of a $^1$H-NMR spectrum of the deuterium-substituted sample.

6 Claims, 1 Drawing Sheet

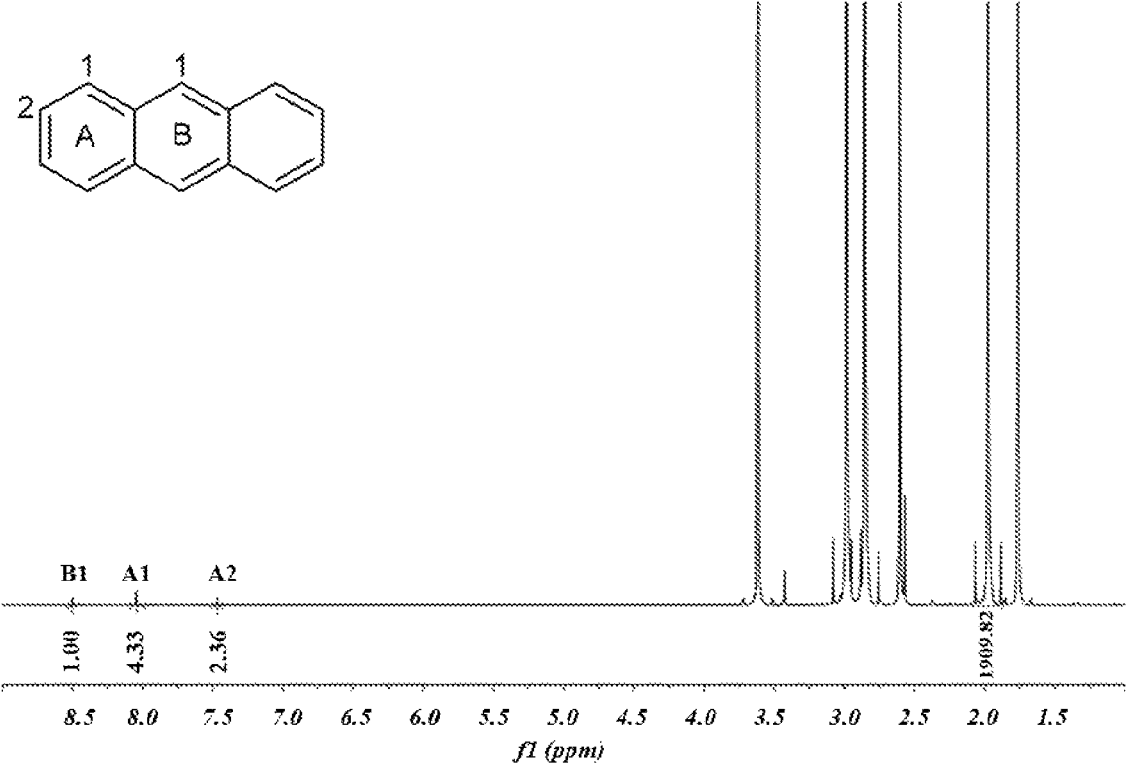

METHOD FOR DETERMINING THE AVERAGE DEUTERIUM SUBSTITUTION RATE

CROSS-REFERENCE TO RELATED APPLICATION(S)

This application claims the benefit of Korean Patent Applications No. 10-2020-0056067 filed on May 11, 2020 and No. 10-2020-0176587 filed on Dec. 16, 2020 with the Korean Intellectual Property Office, the disclosures of which are incorporated herein by reference in their entirety.

BACKGROUND OF THE INVENTION

(a) Field of the Invention

The present disclosure relates to a method for determining the average deuterium substitution rate of a deuterium-substituted sample using information of a $^1$H-NMR spectrum of the deuterium-substituted sample.

(b) Description of the Related Art

In general, an organic light emitting phenomenon refers to a phenomenon converting electrical energy to light energy by using an organic material. The organic light emitting device using the organic light emitting phenomenon has characteristics such as a wide viewing angle, an excellent contrast, a fast response time, excellent luminance, driving voltage and response speed, and thus many studies have proceeded.

The organic light emitting device generally has a structure including an anode, a cathode, and an organic material layer interposed therebetween. The organic material layer frequently have a multilayered structure formed with different materials in order to enhance efficiency and stability of the organic light emitting device, and for example, the organic material layer may be formed of a hole injection layer, a hole transport layer, a light emitting layer, an electron transport layer, an electron injection layer and the like. When a voltage is applied between two electrodes in the structure of the organic light emitting device, holes and electrons are injected to the organic material layer from the anode and the cathode, respectively. And when the injected holes and electrons meet each other, excitons are formed, and light emits when these excitons fall back to the ground state.

There is a continuing demand for developing a new material for organic materials used in such organic light emitting devices, and recently, attempts have been made to improve characteristics such as lifespan of the organic light emitting device through deuterium substitution.

When deuterium is substituted by a deuterium substitution method, the degree of deuterium substitution should be checked. In general, an average deuterium substitution rate of the deuterium-substituted sample should be analyzed. Conventionally, a MS analysis method has been mainly used for this purpose. The MS analysis method is an analytical technique using an $MS_{Max}$ value, which is the molecular weight identified as the largest intensity among the data obtained during analysis. However, since the deuterium-substituted sample actually has molecules having various molecular weights in addition to the molecules having the $MS_{Max}$ value (i.e., has a molecular weight distribution), there is a limitation in analyzing the average deuterium substitution rate.

Accordingly, the present inventors intensively studied the analysis method for the average deuterium substitution rate of the deuterium-substituted sample, and confirmed that the above analysis is possible using information of a $^1$H-NMR spectrum of the deuterium-substituted sample as described later, thereby completing the present invention.

SUMMARY OF THE INVENTION

In the present disclosure, there is provided a method for determining the average deuterium substitution rate of a deuterium-substituted sample using information of a $^1$H-NMR spectrum of the deuterium-substituted sample.

In order to solve the above problems, there is provided the following analysis method:

A method determining the average deuterium substitution rate of a deuterium-substituted sample, including the steps of:

obtaining $^1$H-NMR spectra of the deuterium-substituted sample and a standard sample, respectively (step 1); and calculating an average deuterium substitution rate ([D %]) of the deuterium-substituted sample from the following Equations 1 and 2 using information of the $^1$H-NMR spectra (step 2):

$$D = \frac{SA_H - SA_M * \left(\frac{SA_I}{IS_I} * \frac{IS_W}{SA_W} * \frac{IS_H}{IS_M}\right)}{1 + \left(\frac{SA_I}{IS_I} * \frac{IS_W}{SA_W} * \frac{IS_H}{IS_M}\right)} \qquad \text{[Equation 1]}$$

$$[D\ \%] = (D/SA_H) \times 100 \qquad \text{[Equation 2]}$$

in Equation 1, $IS_W$ is a weight of the standard sample, $IS_I$ is a $^1$H-NMR integration value of a specific peak of the standard sample, $IS_M$ is a molecular weight of the standard sample, $IS_H$ is the number of hydrogens in a molecule in a specific peak of the standard sample, $SA_W$ is a weight of the deuterium-substituted sample, $SA_I$ is a $^1$H-NMR integration value of the deuterium-substituted sample, $SA_M$ is a molecular weight of the deuterium-substituted sample before deuterium substitution, and $SA_H$ is the number of hydrogens in a molecule in the deuterium-substituted sample before deuterium substitution.

The term "average deuterium substitution rate" used in the present disclosure refers to a rate in which deuterium is substituted for hydrogen in the chemical structure of a sample with respect to the entire sample. The present disclosure relates to a method for determining the average deuterium substitution rate of such a deuterium-substituted sample using only the data of a NMR spectrum. To this end, the present disclosure uses 'internal standard' and the difference in atomic weight between $^1$H and $^2$D.

First, because the integrated intensity of a signal in a $^1$H-NMR spectrum is proportional to the amount of nuclides displayed on the signal, quantification can be performed based on the specific signal of the compound to be quantified. In other words, when a standard material that knows its molecular structure is put together in a sample for accurate quantitative analysis, the integrated intensity of a signal of a standard material and the integrated intensity of a specific signal of a compound to be quantified in a $^1$H-NMR spectrum can be obtained. In this case, since the molecular structure and the amount of the standard material are known, quantitative analysis of a compound in the sample is possible. Thus, the standard material that is put together with the sample is referred to as an "internal standard".

In addition, when the molecular weight of the sample before deuterium substitution is C and the number of $^1$H in the chemical structure is H, in the structure substituted with $^2$D, the number of $^1$H decreases (H−D) by the number of substituted-deuterium (D) and the molecular weight increases (C+D) by the number of substituted-deuterium (D). Accordingly, the degree of deuterium substitution can be analyzed by comparing integration values of peaks of the deuterium-substituted sample and the standard sample measured in $^1$H-NMR spectrum.

Hereinafter, the present disclosure will be described in detail for each step.

(Step 1)

The step 1 is to obtain $^1$H-NMR spectra of a deuterium-substituted sample and a standard sample, respectively.

The deuterium-substituted sample refers to a sample in which deuterium is substituted at at least one position where hydrogen can be substituted in the molecular structure. The deuterium-substituted sample may be commercially available, or may be prepared by substituting with deuterium according to a conventionally known method.

As the standard sample, the type is not particularly limited as long as a characteristic peak appears in the $^1$H-NMR spectrum. Preferably, a material in which the characteristic peak is prominent in the $^1$H-NMR spectrum is used. In addition, the standard sample is preferably a material with low volatility. For example, dimethyl acetamide may be used as the standard sample.

The $^1$H-NMR spectrum is for obtaining an integration value of a peak at each position in Equation 1 to be described later. Therefore, the method is not particularly limited as long as the peak at each position in the deuterium-substituted sample can be obtained.

Preferably, in step 1, the deuterium-substituted sample and the standard sample are mixed, and then the $^1$H-NMR spectrum thereof is obtained. Preferably, the deuterium-substituted sample and the standard sample are mixed in a weight ratio of 1:100 to 100:1, more preferably in a weight ratio of 1:10 to 10:1.

Meanwhile, the weight of the deuterium-substituted sample and the weight of the standard sample used to obtain the $^1$H-NMR spectra in step 1 are referred to as SA$_W$ and IS$_W$, respectively, which will be used in Equation 1 to be described later.

(Step 2)

The step 2 is to analyze the average deuterium substitution rate of the deuterium-substituted sample using the information obtained in step 1.

Specifically, the average deuterium substitution rate of the deuterium-substituted sample may be analyzed using Equations 1 and 2 above. For convenience of explanation, the following Equations 1 and 2 will be described in detail by taking deuterium-substituted anthracene as an example and dimethyl acetamide as a standard sample.

First, a $^1$H-NMR integration value of a specific peak of the standard sample is obtained. And, from this, a rate of the number of moles of the standard sample and the integration value of the specific peak can be known. Subsequently, a rate of the number of moles of the deuterium-substituted sample and the $^1$H-NMR integration value is the same as that of the standard sample, and thus this can be summarized by the following equation.

$$\frac{IS_W}{IS_M} : \frac{SA_W}{(SA_M + D)} = \frac{IS_I}{IS_H} : \frac{SA_I}{(SA_H - D)}$$

In the above equation, definitions other than D are as previously defined, and D refers to the number of substituted-deuterium in the molecule. That is, in the deuterium-substituted sample, the molecular weight increases by the number of substituted-deuterium (SA$_M$+D), and the $^1$H-NMR integration value decreases by the number of substituted-deuterium (SA$_H$−D). When the above equation is rearranged to get an equation for D, it becomes Equation 1 above.

Since the D value obtained in Equation 1 refers to the number of deuterium present in the deuterium-substituted sample, the average deuterium substitution rate of the deuterium-substituted sample can be analyzed by dividing the D value by the number of hydrogens (SA$_H$) in the molecule in the deuterium-substituted sample before deuterium substitution as in Equation 2.

As described above, the present disclosure can analyze the average deuterium substitution rate of the deuterium-substituted sample using information of the $^1$H-NMR spectrum. The analysis method according to the present disclosure has an advantage that a sample before deuterium substitution of the deuterium-substituted sample is not required. In addition, there is an advantage that the average deuterium substitution rate of the deuterium-substituted sample can be analyzed using only the $^1$H-NMR spectrum without any other analysis method.

Further, there is provided a method for preparing an organic light emitting device comprising using the deuterium-substituted sample.

BRIEF DESCRIPTION OF THE DRAWINGS

FIG. 1 is a $^1$H-NMR spectrum measured in Example of the present disclosure.

DETAILED DESCRIPTION OF THE EMBODIMENTS

Hereinafter, the embodiment of the present invention will be described in more detail in the following examples. However, these examples are for illustrative purposes only, and the invention is not intended to be limited by these examples.

Example: Analysis of Average Deuterium Substitution Rate of Anthracene

The following experiment was performed using deuterium-substituted anthracene (Anthracene-d10; manufactured by Sigma-Aldrich; Product number 176591; CAS number 1719-06-8).

Deuterium-substituted anthracene (3.14 mg) and dimethyl acetamide (DMAc; 10.97 mg) as a standard sample were accurately quantified and mixed, and then $^1$H-NMR spectrum was measured. The results are shown in FIG. 1, and the measurement conditions are as follows.

pulse sequence=zg30
number of scan (ns)=32
relaxation delay (d1)=10.0 sec
acquisition time (aq)=2.3 sec
temperature=298 K In FIG. 1, hydrogen substituted at carbon 1 among the peaks of the standard sample was used as a reference. The information in Table 1 below was obtained from FIG. 1.

TABLE 1

| | Deuterium-substituted anthracene | | Dimethyl acetamide |
|---|---|---|---|
| $SA_W$: Weight (mg) | 3.14 | $IS_W$: Weight (mg) | 10.97 |
| $SA_I$: ¹H-NMR integration value | 7.69 | $IS_I$: ¹H-NMR integration value of specific peak | 1908.92 |
| Molecular weight | 178 + D | $IS_M$: Molecular weight | 87 |
| Number of hydrogens in molecule | 10 − D | $IS_H$: Number of hydrogens in molecule in specific peak | 3 |
| $SA_M$: Molecular weight before deuterium substitution | 178 | | |
| $SA_H$: Number of hydrogens before deuterium substitution | 10 | | |

The D value was 9.91 by substituting the information obtained above into Equation 1, and the average deuterium substitution rate of anthracene was analyzed to be 99.1% by substituting the information obtained above into Equation 2.

What is claimed is:

1. A method for determining the average deuterium substitution rate of a deuterium-substituted sample, comprising:
   obtaining ¹H-NMR spectra of the deuterium-substituted sample and a standard sample, respectively (step 1), wherein the deuterium-substituted sample and the standard sample is mixed in a weight ratio of 1:100 to 100:1; and
   calculating an average deuterium substitution rate ([D %]) of the deuterium-substituted sample from the following Equations 1 and 2 using information of the ¹H-NMR spectra (step 2):

$$D = \frac{SA_H - SA_M * \left(\frac{SA_I}{IS_I} * \frac{IS_W}{SA_W} * \frac{IS_H}{IS_M}\right)}{1 + \left(\frac{SA_I}{IS_I} * \frac{IS_W}{SA_W} * \frac{IS_H}{IS_M}\right)}$$ [Equation 1]

$$[D\%] = (D / SA_H) \times 100$$ [Equation 2]

wherein Equation 1,
$IS_W$ is a weight of the standard sample,
$IS_I$ is a ¹H-NMR integration value of a specific peak of the standard sample,
$IS_M$ is a molecular weight of the standard sample,
$IS_H$ is a number of hydrogens in a molecule in a specific peak of the standard sample,
$SA_W$ is a weight of the deuterium-substituted sample,
$SA_I$ is a ¹H-NMR integration value of the deuterium-substituted sample,
$SA_M$ is a molecular weight of the deuterium-substituted sample before deuterium substitution, and
$SA_H$ is a number of hydrogens in a molecule in the deuterium-substituted sample before deuterium substitution.

2. The method of claim 1,
wherein the step 1 is performed by mixing the deuterium-substituted sample and the standard sample, and then obtaining a ¹H-NMR spectrum thereof.

3. The method of claim 2,
wherein the deuterium-substituted sample and the standard sample is mixed in a weight ratio of 1:10 to 10:1.

4. The method of claim 1,
wherein the $SA_W$ is a weight of the deuterium-substituted sample used to obtain the ¹H-NMR spectra in step 1, and
$IS_W$ is a weight of the standard sample used to obtain the ¹H-NMR spectra in step 1.

5. The method of claim 1,
wherein the standard sample is dimethyl acetamide.

6. The method of claim 1,
wherein the deuterium-substituted sample is deuterium-substituted anthracene.

* * * * *